US00PP36724P2

(12) United States Plant Patent
Carrella

(10) Patent No.: US PP36,724 P2
(45) Date of Patent: Jun. 3, 2025

(54) ***CALIBRACHOA* PLANT NAMED 'KLECA23958'**

(50) Latin Name: ***Calibrachoa* sp.**
Varietal Denomination: KLECA23958

(71) Applicant: KLEMM + SOHN GMBH & CO. KG, Stuttgart (DE)

(72) Inventor: Angelo Carrella, Palma Campania (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/766,385

(22) Filed: Jul. 8, 2024

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 6/821; A01H 5/02
See application file for complete search history.

*Primary Examiner* — Keith O. Robinson
(74) *Attorney, Agent, or Firm* — Weatherly IP Solutions LLC; James M. Weatherly

(57) ABSTRACT

A new *Calibrachoa* plant particularly distinguished by having pink flowers, with vigorous plant growth, and a semi-trailing plant habit, is disclosed.

1 Drawing Sheet

Genus and species: *Calibrachoa* sp.
Variety denomination: 'KLECA23958'.

BACKGROUND OF THE NEW PLANT

The present invention comprises a new and distinct variety of *Calibrachoa*, botanically known as *Calibrachoa* sp., and hereinafter referred to by the variety name 'KLECA23958'. 'KLECA23958' originated from a controlled-cross between the proprietary female *Calibrachoa* variety 'CA-2019-FV1211' (unpatented) and the male *Calibrachoa* variety 'KLECA20810' (U.S. Plant Pat. No. 33,989).

In August 2019, two *Calibrachoa* parental lines, the female variety 'CA-2019-FV1211' and the male variety 'KLECA20810' were crossed via a controlled-cross in Stuttgart, Germany and seeds were obtained. The seeds were sown and plants were grown for evaluation. A plant line was selected in May 2020 and subsequently named 'KLECA23958'. In May 2019, 'KLECA23958' was first vegetatively propagated by cuttings. 'KLECA23958' was found to reproduce true to type in successive generations of asexual propagation via cuttings.

SUMMARY

The following are the most outstanding and distinguishing characteristics of this new variety when grown under normal horticultural practices in Stuttgart, Germany.

1. Pink flowers;
2. A vigorous growth habit; and
3. Semi-trailing plant habit.

DESCRIPTION OF THE PHOTOGRAPH

This new *Calibrachoa* plant is illustrated by the accompanying photograph which shows a close-up of the whole plant. The photograph is of a 12-week-old-plant grown in a greenhouse Stuttgart, Germany in May 2023. The colors shown are as true as can be reasonably obtained by conventional photographic procedures.

DESCRIPTION OF THE NEW VARIETY

The following detailed descriptions set forth the distinctive characteristics of 'KLECA23958'. The data which define these characteristics were collected from asexual reproductions carried out in Latina, Italy. Data was collected on 15-week old plants after transplant in Latina, Italy. Color references are to The R.H.S. Colour Chart of The Royal Horticultural Society of London (R.H.S.), 5$^{th}$ edition (2007).

Classification:
- *Family*.—Solanaceae.
- *Species*.—*Calibrachoa* sp.
- *Common name*.—*Calibrachoa*.

Parentage:
- *Female*.—'CA-2019-FV1211' (unpatented).
- *Male*.—'KLECA20810' (U.S. Plant Pat. No. 33,989).

Plant description:
- *Life cycle*.—Annual.
- *Form*.—Short-lived subshrub.
- *Habit*.—Semi-trailing.
- *Height* (*from soil line to top of foliage*).—9.6 cm.
- *Spread*.—38.2 cm.

Propagation:
- *Type cuttings*.—Tip cutting.
- *Time to produce a rooted cutting*.—3 weeks.

Stems:
- *Stem color*.—RHS 145B.
- *Pubescence color*.—RHS 155A.
- *Stem diameter*.—0.11 cm.
- *Stem length*.—From soil line to first node: 1.1 cm. Total length: 22.2 cm.
- *Internode length*.—1.2 cm.

Leaves:
- *Arrangement*.—Even pinnate.
- *Shape*.—Cuneate.
- *Apex*.—Obtuse.

*Base*.—Acute.
*Margin*.—Ciliate.
*Surface pubescence*.—Present.
*Pubescence color*.—RHS 155A.
*Venation color*.—Upper surface: RHS 138B. Lower surface: RHS 137B.
*Length*.—2.9 cm (mature leaves).
*Width*.—1.1 cm (mature leaves).
*Color*.—Upper surface: RHS 137B. Lower surface: RHS 137D.
*Fragrance*.—Absent.

Flowers:
*Flowering habit*.—Single flower.
*Flower type*.—Single.
*Flowering requirements*.—A minimum of sun light is required.
*Duration of flowers*.—7 to 10 days.
*Corolla*.—Smooth.
*Shape*.—Funnel form.
*Fragrance*.—Absent.

Flower buds:
*Surface*.—Pubescent.
*Length*.—2.2 cm.
*Diameter*.—0.3 cm.
*Shape*.—Irregular to oblong.
*Color*.—RHS 69B (top buds) 145C (base buds).

Peduncle:
*Length*.—2.6 cm.
*Diameter*.—Less than 0.1 cm.
*Color*.—RHS 144B.
*Anthocyanin*.—Absent.

Flower description:
*Flower depth*.—2.3 cm.
*Flower tube length*.—1.6 cm.
*Flower tube diameter*.—0.8 cm.
*Flower diameter*.—3.3 cm.
*Lobing*.—Weak.
*Conspicuousness of the veins of the flower*.—Absent.
*Pedicel length*.—2.6 cm.
*Pedicel color*.—RHS 144B.

Sepals:
*Shape*.—Ovate.
*Apex*.—Obtuse.
*Margin*.—Ciliate.
*Length*.—1.3 cm.
*Diameter*. 0.25 cm.
*Sepal color*.—Upper surface: RHS 138A. Lower surface: RHS 138B.

Petals:
*Shape*.—Obcordate.
*Length*.—1.3 cm.
*Apex*.—Obtuse.
*Margin*.—Entire.
*Base*.—Fuse in the tube.
*Pubescence*.—Absent.
*Lobe length*.—1.3 cm.
*Lobe width*.—1.2 cm.
*Color*.—Lobe color: Upper surface: RHS N155 B (border), RHS N74B and RHS N34A. Center, and RHS 7A stripes. Lower surface: RHS N155B. Corolla tube color: Inner: RHS 7A. Outer: RHS 2B.
*Fragrance*.—Absent.

Reproductive organs:
*Stamen number*.—5.
*Stamen color*.—Anther color: RHS 13B. Filament color: RHS 12C. Pollen color: RHS 12A. Pollen amount: Moderate.
*Placenta arrangement*.—Ovate.
*Pistil number*.—1.
*Pistil length*.—0.7 cm.
*Stigma color*.—RHS 145A.
*Style length*.—0.6 cm.
*Style color*.—RHS 145B.

Fruit/seed set: None observed.

Disease/insect resistance: No pests and disease were observed.

COMPARISON WITH PARENTAL LINES AND KNOWN VARIETY

'KLECA23958' is distinguished from its parents as described in Table 1 and Table 2:

TABLE 1

Comparison with Parental Lines

| Trait | Variety 'KLECA23958' | Female parent |
|---|---|---|
| Earliness | 40 days from potting to flowering | 44 days from potting to flowering |

TABLE 2

Comparison with Male Parental Line

| Trait | Variety 'KLECA23958' | Male Parent |
|---|---|---|
| Vigor | More vigorous than the male parent | Less vigorous than 'KLECA23958' |

'KLECA23958' is most similar to the *Calibrachoa* plant named 'KLECA22822' (unpatented). Differences between the two varieties are described in Table 3:

TABLE 3

Comparison with Similar Variety

| Trait | Variety 'KLECA23958' | Commercial line 'KLECA22822' |
|---|---|---|
| Main flower color | Pink | Blue |

I claim:

1. A new and distinct variety of *Calibrachoa* plant named 'KLECA23958' as shown and described herein.

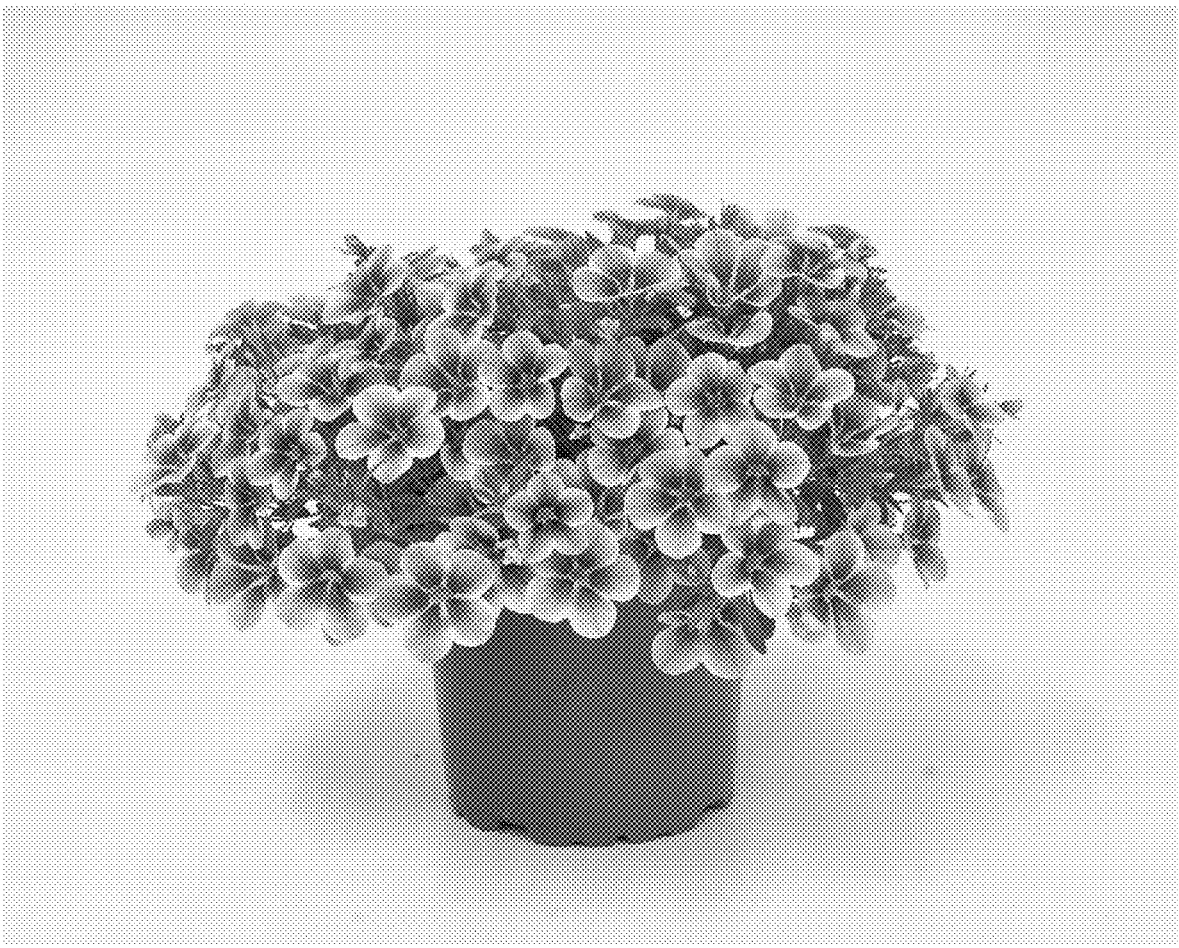

* * * * *